United States Patent
Jean et al.

(10) Patent No.: US 6,264,928 B1
(45) Date of Patent: Jul. 24, 2001

(54) USE OF SHOGAOLS AND GINGEROLS FOR PREPARING DEODORANT COMPOSITIONS

(75) Inventors: Daniel Jean, Vic-le-Comte; Léon Cariel, Paris, both of (FR)

(73) Assignee: Societe d'Etudes et de Recherches en Pharmacognosie, Paris (FR)

( * ) Notice: Subject to any disclaimer, the term of this patent is extended or adjusted under 35 U.S.C. 154(b) by 0 days.

(21) Appl. No.: 09/341,383

(22) PCT Filed: Jan. 8, 1998

(86) PCT No.: PCT/FR98/00025

§ 371 Date: Sep. 7, 1999

§ 102(e) Date: Sep. 7, 1999

(87) PCT Pub. No.: WO98/30201

PCT Pub. Date: Jul. 16, 1998

(30) Foreign Application Priority Data

Jan. 9, 1997 (FR) .................................................. 97 00142
Jan. 9, 1997 (FR) .................................................. 97 00143

(51) Int. Cl.$^7$ ................................ A61K 7/32; A61K 7/00

(52) U.S. Cl. ............................................. 424/65; 424/401

(58) Field of Search ............................... 424/65, 76.1, 401

(56) References Cited

FOREIGN PATENT DOCUMENTS

| 334967 | 10/1989 | (EP) . |
| 750908 | 1/1997 | (EP) . |
| WO 93/23061 | 11/1993 | (WO) . |

OTHER PUBLICATIONS

Patent Abstracts of Japan, vol. 13, No. 137 (C–582), Publication No. JP 63 303908 to Aranami Tsuneo.

Database WPI, Derwent Publications Ltd., XP002044592, Week 9729, Publication No. JP 09 124 677 to Eba Kashohin KK.

Database WPI, Derwent Publications Ltd., XP002044593, Week 8934, Publication No. JP 01 180 817 to Morishita Jintan KK.

(List continued on next page.)

Primary Examiner—Shelley A. Dodson
Assistant Examiner—Konata M. George
(74) Attorney, Agent, or Firm—Alston & Bird LLP

(57) ABSTRACT

A method is provided for suppressing body odors in a human by administering orally to the human or applying to the skin of the human, at least one compound chosen from the group consisting of shogaols and gingerols. The compound corresponds to the general formula:

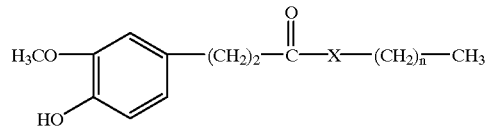

Figure 1:
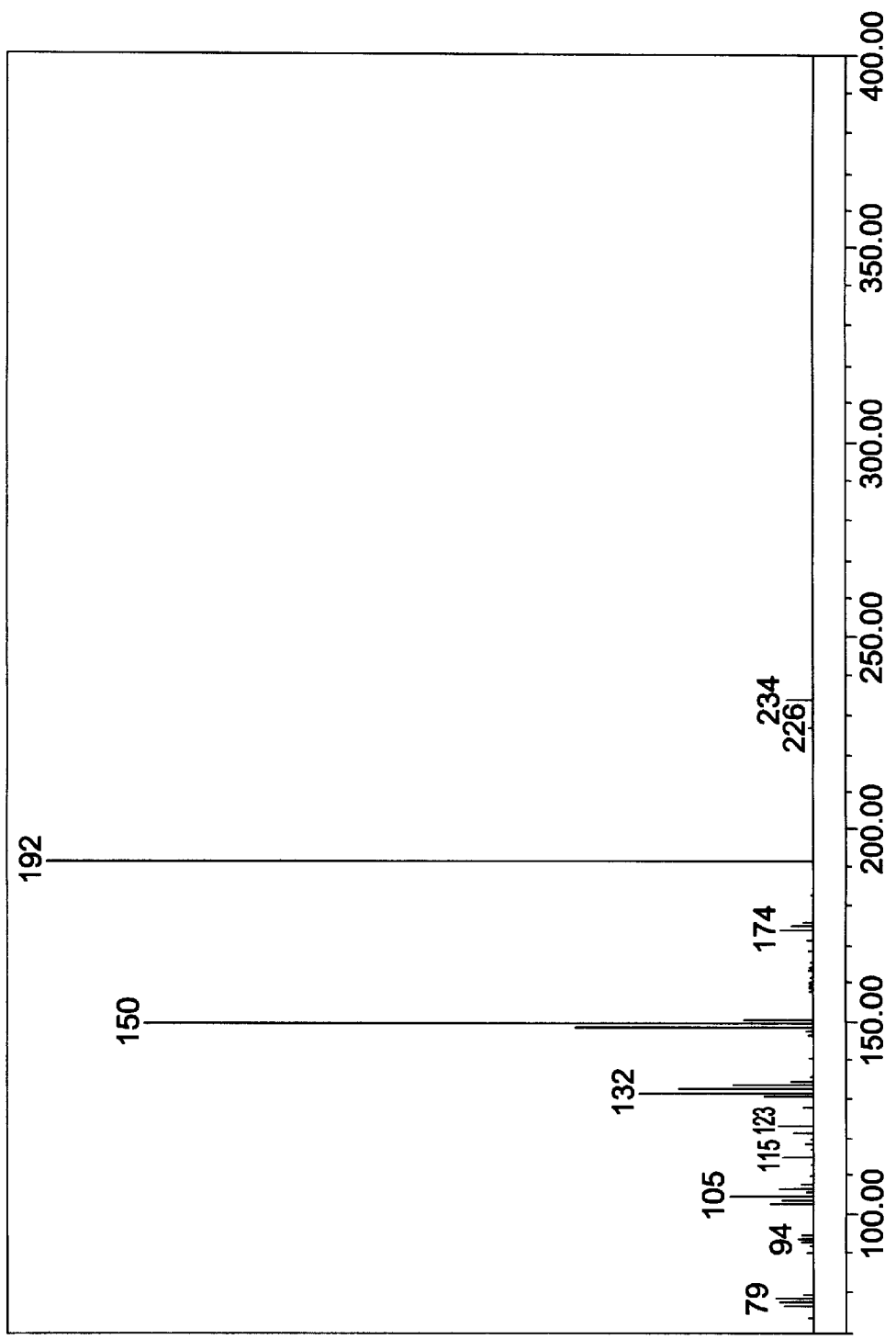

in which X represents:

either —CH=CH—, in which case n is equal to 1, 2, 4, 6, or 8;

—CH$_2$—CH(OH)—, in which case n is equal to 2, 4, 6 or 8.

22 Claims, 1 Drawing Sheet

OTHER PUBLICATIONS

STN, Serveur de Bases de Donnees, XP002044589, vol. 101, AN=235404.

Patent Abstracts of Japan, vol. 95, No. 010, Publication No. JP 07 171209 to Matsushita Electric Works.

STN, Serveur de Bases de Donnees, XP002044590, AN=90018412.

STN, Serveur de Bases de Donnees, XP002044591, vol. 106, AN=89987.

Database WPI, Derwent Publications Ltd., XP002066395, Week 9439, Publication No. JP 06 239 736 to Pola Chem Ind. Inc.

Database WPI, Derwent Publications Ltd., XP002066396, Week 9431, Publication No. JP 06 183 959 to Pola Chem Ind. Inc.

Database WPI, Derwent Publications Ltd., XP002066397, Week 8217, Publication No. JP 57 046 914 to Tsumura Juntendo KK.

USE OF SHOGAOLS AND GINGEROLS FOR PREPARING DEODORANT COMPOSITIONS

The present invention relates to the use of shogaols and gingerols for the preparation of deodorant compositions.

The odour of the skin is produced by the secretions of the sweat glands and the sebaceous glands.

The sweat glands produce sweat which consists of water containing a larger or smaller amount of mineral salts and organic substances (lactic acid, urea, etc.), while the sebaceous glands secrete sebum which is mainly formed from fatty substances: cholesterol and its esters, steric acid and palmitic acid and their esters.

Studies [Shelley et al., Arch. *Dermatol. Syphilol.*, 68, 430 (1973)] have shown that the sebaceous and sweat secretions are odourless at the time of production. The odours are produced subsequently by the action of commensal skin bacteria, this action being exerted essentially on apocrine sweat and the sebum on account of their richness in organic substance. Ecrine seat, which is more abundant but has a poorer organic matter content than apocrine sweat, plays only a small part in the creation of odours, although it can play an indirect role by promoting the dispersion of the apocrine sweat components by way of its volume.

Thus, the decomposition of the secretions of the sweat glands and sebaceous glands by the bacterial flora naturally present on the skin, probably in combination with a decomposition of the proteins of the horny layer, gives rise to many highly odorous molecules.

Three types of product which can be used exclusively externally are currently available to counter this phenomenon, which exists over the entire surface of the body but which is particularly pronounced in the pilous regions (armpits, inguinal folds, pubic region, etc.) and palmoplantar regions:
 products known as antiperspirants, which are aimed at reducing the production of sweat,
 producing which are aimed at limiting the local microbial proliferation and thus the decomposition of the skin secretions, and
 products which are aimed at neutralizing, as they are produced, the substances derived from this decomposition which are responsible for the unpleasant odours.

Although, in general, these products show a certain level of efficacy, they have the drawback, on account of their formulation and/or their presentation, of being adapted and, consequently, limited to application to a specific region of the body: armpits, genital region or feet, whereas it would be highly desirable to have available products for universal use, allowing treatment of all the regions of the body which are concerned.

Moreover, certain individuals suffer from veritable perspiration disorders such as ephidrosis, which corresponds to an abnormally high production of sweat, or bromidrosis, which is characterized by the production of particularly fetid sweat, and which are a considerable indisposition for sufferers themselves and for people in their vicinity. For these individuals, the current absence of products capable of systemically treating their complaint is a very real handicap.

Lastly, besides the fact that a body hygiene product needs to be free of toxicity, in particular when it is a deodorant, the suspicion expressed to an every greater extent by many consumers towards products of chemical origin drives them to select by preference products of natural origin.

The problem consequently arises of providing products which are capable of effectively preventing the production of body odours and of doing so both when they are administered systemically and when they are used locally, which can, in the latter case, be applied to any region of the body, which, furthermore, lack toxicity and which also have the advantage of being products of natural origin.

In the context of their studies, the inventors have now found that shogaols and gingerols, compounds which correspond to the general formula (I) below:

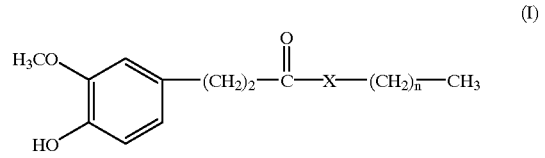

(I)

in which:
 X represents —CH═CH— in the case of shogaols, while
 X represents —CH$_2$—CH(OH)— in the case of gingerols,
and which are present in plants of the Zingiberacea family, are, unexpectedly, endowed with pronounced deodorant properties, not only when they are applied to the skin but also when they are ingested orally, while at the same time being non-toxic, which makes them advantageous for the preparation of deodorant compositions for the body, which can be used systemically or locally.

A subject of the present invention is thus the use of at least one compound chosen from the group which comprises shogaols and gingerols for the preparation of a deodorant composition.

In accordance with the invention, the compound is preferably chosen from the shogaols corresponding to the general formula (I) mentioned above in which, with X representing —CH═CH—, n is equal to 1, 2, ,4, 6 or 8, and which are respectively known as [3]-shogaol, [4]-shogaol, [6]-shogaol, [8]-shogaol and [10]-shogaol, and the gingerols which correspond to the general formula (I) mentioned above in which, with X representing —CH$_2$—CH(OH)—, n is equal to 2, 4, 6 or 8, and which are known under the respective names [4]-gingerol, [6]-gingerol, [8]-gingerol and [10]-gingerol.

Shogaols and gingerols can be extracted, by any extraction process known per se, from the rhizomes of many Zingiberacea plants and, more particularly, from those belonging to the genera Alpinia and Zingiber. As examples, [3]-shogaol, [6]-shogaol and [8]-shogaol can be extracted from plants of the genus Alpinia, such as *Alpinia galanga* or *Alpinia officinarum*, while [4]-shogaol, [10]-shogaol and the gingerols can be extracted from plants of the genus Zingiber, such as *Zingiber officinalis, Zingiber cassumunar* and *Zingiber zerumbet*.

Shogaols and gingerols can also be obtained by chemical synthesis, for example according to the processes described by Banno and Mukaiyama, *Bull, Chem.* Soc. Japan, 49 (5), 1453–1454 (1976).

According to a first preferred embodiment of the invention, the compound is used in the form of a crude or purified extract of a plant belonging to the Zingiberacea family, the said extract optionally being combined with one or more other active substances and/or which one or more suitably selected excipients.

According to one advantageous arrangement of this preferred embodiment, the crude Zingiberacea extract contains an amount of compound of between about 1% and about 5% by weight relative to the dry weight of the said extract.

In accordance with the invention, such a crude extract is obtained from fresh or dry rhizomes of the said plant:

by macerating ground material of these rhizomes at a temperature of between 10 and 35° C., followed by one or more extractions of this ground materials at reflux, or by subjecting ground material of the said rhizomes to percolation at a temperature of between 10 and 35° C., each of these operations (maceration, extractions at reflux and percolation) being performed using a suitable organic solvent or a mixture of suitable organic solvents and, if desired, by removing the solvent(s) from the extract thus obtained in order to obtain a dry extract.

The maceration of the ground rhizome material, prior to its extraction, mainly has the effect of improving the contact between the plant tissues and the extraction solvent(s). Its duration can be between about twelve hours and one week depending on the state of freshness of the rhizomes used.

For the maceration, extractions at reflux and percolation of the ground material, water-miscible organic solvents are preferably used, the solvents having a relative low boiling point so as to be easy to remove subsequently by simple evaporation, such as ethanol, methanol or acetone, or mixtures thereof with water. However, since shogaols and gingerols are soluble in many organic solvents, it is also possible to use other organic solvents, such as ethyl acetate, ethyl ether, chloroform or methylene chloride.

According to another advantageous arrangement of this preferred embodiment of the invention, the purified Zingiberacea extract contains an amount of compound at least equal to 75% by weight relative to the dry weight of the said extract.

Advantageously, such a purified extract is obtained:

by subjecting a crude extract as defined above, after optional removal of the solvent(s) it contains and/or its uptake in water, to one or more counter-current extractions using a water-immiscible organic solvent or a mixture of water-immiscible organic solvents and, if desired, by removing the solvent(s) from the extract thus obtained in order to obtain a dry extract.

The water-immiscible organic solvent(s) which is (are) useful for carrying out the said counter-current extractions is (are) chosen in particular from ethyl acetate, ethyl ether, chloroform and methylene chloride, and mixtures thereof.

In a particularly preferred manner, whether it is crude or purified, the extract is an extract of a Zingiberacea plant chosen from the group which comprises *Alpinia galanga, Alpinia officinarum, Zingiber officinalis, Zingiber cassumunar* and *Zingiber zerumbet*.

According to another preferred embodiment of the invention, the deodorant composition is formulated for oral administration, for example in the form of a powder, a drinkable suspension or solution, a syrup, tablets or gel-capsules.

According to yet another preferred embodiment of the invention, the deodorant composition is formulated for local application, for example in the form of a dermal powder, solution, suspension, gel or cream.

According to yet another embodiment of the invention, the deodorant composition is a pharmaceutical composition which comprises the compound as active principle, optionally combined with one or more other active principles, and at least one pharmaceutically acceptable excipient. Such a pharmaceutical composition, which can be administered systemically and in particular orally, or locally, finds application in the treatment of dyshidrosis and, more particularly, that of bromidrosis.

As a variant, the deodorant composition is a cosmetic composition which comprises the compound as active substance, optionally combined with one or more other active substances, and at least one suitably selected excipient.

According to yet another variant, the deodorant composition is a dietary composition which comprises the compound as active substance, optionally combined with one or more other active substances, and at least one suitable selected excipient.

Such cosmetic and dietary compositions can advantageously be used as body deodorants to prevent the production of unpleasant odours associated in particular with perspiration.

The invention encompasses, for the abovementioned use, both shogaols known per se, such as [4]-shogaol, [6]-shogaol, [8]-shogaol and [10]-shogaol [Connell and Sutherland, Aust. J. Chem., 22 (5), 1033–1043 (1969)], but whose deodorant properties were neither known nor suggested hitherto, and a new shogaol which is [3]-shogaol, corresponding to formula (II) below:

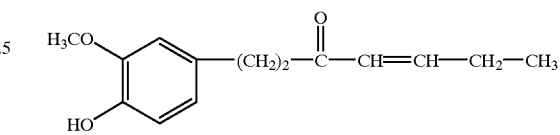

(II)

and which represents, on account of its particularly pronounced deodorant properties, the shogaol preferably used in the invention.

As mentioned above, [3]-shogaol can be obtained in particular from a plant of the genus Alpinia, by means of a process comprising:

the preparation of a crude extract from fresh or dry rhizomes of this plant, the purification of the crude extract thus obtained, followed by chromatographic separation of this [3]-shogaol from the other shogaols which may be present in the purified extract.

A subject of the invention is also a crude extract of a plant belonging to the genus Alpinia, characterized in that it contains an amount of [3]-shogaol of between about 1% and about 5% by weight relative to the dry weight of the said extract.

In accordance with the invention, this extract is obtained from fresh or dry rhizomes of the said plant:

by macerating ground material of these rhizomes at a temperature of between 10 and 35° C., followed by one or more extractions of this ground material at reflux, or by subjecting ground material of the said rhizomes to percolation at a temperature of between 10 and 35° C., each of these operations (maceration, extractions at reflux and percolation) being performed using a suitable organic solvent or a mixture of suitable organic solvents and, if desired, by removing the solvent(s) from the extract thus obtained in order to obtain a dry extract.

According to a preferred embodiment of the invention, the said crude extract is an extract of *Alpinia galanga*.

A subject of the invention is also a purified extract of a plant belonging to the genus Alpinia, characterized in that it contains an amount of [3]-shogaol at least equal to 75% by weight relative to the dry weight of the said extract.

Advantageously, this purified extract is obtained:
by subjecting a crude extract as defined above, after optional removal of the solvent(s) it contains and/or its uptake in water, to one or more counter-current extractions using a water-immiscible organic solvent or a mixture of water-immiscible organic solvents and, if desired,
by removing the solvent(s) from the extract thus obtained in order to obtain a dry extract.

This purified extract is preferably an extract of *Alpinia galanga*.

Such crude or purified extracts of Alpinia have been themselves found to be endowed with pronounced deodorant properties when they are administered systemically or applied locally, while at the same time being free of toxicity, and are consequently particularly suitable for the preparation of a deodorant composition in accordance with the invention. To this end, they can be used either in their native form as dry powders or aqueous or alcoholic solutions, or in the form of more complex formulations, optionally combined with other active substances.

A subject of the present invention is also a deodorant composition, characterized in that it comprises [3]-shogaol as active substance.

According to a first embodiment, this composition is a pharmaceutical composition which comprises [3]-shogaol as active principle, optionally combined with one or more other active principles and at least one pharmaceutically acceptable excipient.

According to another embodiment, this composition is a cosmetic composition which comprises [3]-shogaol as active substance, optionally combined with one or more other active substances, and at least one suitably selected excipient.

According to yet another embodiment, this composition is a dietary composition which comprises [3]-shogaol as active substance, optionally combined with one or more other active substances, and at least one suitably selected excipient.

In addition to the preceding arrangements, the invention also comprises other arrangements which will emerge from the remainder of the description which follows, which refers to examples for the preparation of extracts of rhizomes from plants of the Zingiberacea family which can be used in accordance with the invention, to an example of the production of [3]-shogaol and examples for the demonstration of the deodorant activities of these extracts and of this [3]-shogaol, and which refers to the attached FIG. 1 which shows the mass spectrum of [3]-shogaol.

It goes without saying, however, that these examples are given purely for the purpose of illustrating the subject of the invention, of which they in no way constitute a limitation.

EXAMPLE 1

PREPARATION OF A CRUDE EXTRACT OF *ALPINIA GALANGA* RHIZOMES

One kilogram of fresh *Alpinia galanga* rhizomes is ground coarsely, taking care not to cause excessive heating of the ground parts. The water content of the ground material thus obtained is determined and it is macerated in 7 litres of ethanol whose titer is chosen such that, taking the water content of the ground material into account, the maceration solvent is 50% ethanol.

After macerating for 24 hours at about 20° C., the ground material is extracted at reflux with the maceration solvent for 30 minutes. This solvent is removed and replaced with an equal weight of 50% ethanol, and the ground material is extracted at reflux for a further 30 minutes. The operation is repeated once.

The 3 extracts obtained are combined (thus constituting a volume of about 19 litres), filtered through paper and then evaporated to dryness under reduced pressure.

A residue which weighs about 50 g if obtained, i.e. an approximate yield of 30% relative to the dry weight of the rhizomes. This extract contains the various shogaols present in the *Alpinia galanga* rhizomes ([3]-shogaol, [6]-shogaol and [8]-shogaol) and its content of [3]-shogaol is generally between 1 and 5% (w/w) depending on the rhizomes used.

EXAMPLE 2

PREPARATION OF A PURIFIED EXTRACT OF *ALPINIA GALANGA* RHIZOMES 50 g of a crude extract, prepared in accordance with Example 1, are taken up in 1 litre of distilled water and the mixture is boiled for 1 minute with constant stirring. Stirring is continued until complete homogenization of this extract is obtained, and the mixture is allowed to cool. It is then subjected to 4 successive counter-current extractions, each performed with 100 ml of ethyl ether.

The ether solutions are combined; anhydrous sodium sulphate is added to remove the water contained therein; they are filtered through paper and evaporated to dryness under reduced pressure.

A residue is thus obtained which weighs 6.8 g, i.e. a yield of about 4% relative to the dry weight of the rhizomes. This extract, which mainly contains [3]-shogaol, has a [3]-shogaol content which is generally greater than 75% (w/w).

EXAMPLE 3

PRODUCTION OF [3]-SHOGAOL

[3]-Shogaol can be obtained from *Alpinia galanga* rhizomes by preparing a crude extract of these rhizomes in accordance with Example 1, followed by purifying this extract in accordance with Example 2 and then subjecting the extract thus purified to successive elutions on columns of silica gel, for example in the following way.

100 g of a silica gel G60 and 500 ml of chloroform are added, with constant stirring, to 10 g of a purified extract, prepared in accordance with Example 2. Once this mixture is homogenous, it is evaporated to dryness under reached pressure so as to obtained a powder.

This powder is placed at the top of a column 10 cm in diameter and 50 cm in height, also containing silica gel G60 in petroleum ether. Elution is carried out first with petroleum ether until the residue is less than 0.1% (about 10 litres of petroleum ether are required to reach this stage), then with 12 litres of benzene and finally with 8 litres of chloroform.

The chloroform phase is evaporated to dryness under reduced pressure, to give about 2.3 g of residue. This residue is then subjected to preparation chromatography on a column 5 cm in diameter and 20 cm in height, filled with C18 silica gel, and using a water/acetonitrile mixture (70/30) as elution gradient. The fraction containing [3]-shogaol is eluted in a time of between 5 and 7 minutes at a flow rate of 30 ml/min.

The [3]-shogaol can be identified by high pressure liquid chromatography (HPLC) coupled to mass spectrometry.

FIG. 1 shows the mass spectrum of the [3]-shogaol obtained with a Waters Integrity® spectrometer with ionization by electron impact, coupled to HPLC carried out on a Nucleosil® column (4.6×150 mm, 3 μm) with isocratic elution with an isopropanol/cyclohexane mixture (10/90).

EXAMPLE 4

PREPARATION OF A CRUDE EXTRACT OF ZINGIBER OFFICINALIS RHIZOMES

Using a procedure identical to the one described in Example 1, and starting with one kilogram of fresh *Zingiber officinalis* rhizomes, a residue is obtained weighing about 52 g, i.e. an approximate yield of 35% relative to the dry weight of the rhizomes.

This extract, which contains the gingerols present in the *Zingiber officinalis* rhizomes ([6]-gingerol, [8]-gingerol and [10]-gingerol), has a gingerol content which is generally between 1 and 5% (w/w) depending on the rhizomes used.

EXAMPLE 5

PREPARATION OF A PURIFIED EXTRACT OF ZINGIBER OFFICINALIS RHIZOMES

By subjecting 50 g of a crude extract prepared in accordance with Example 4 to purification under conditions identical to those described in Example 2, a residue is obtained which weighs 8.2 g, i.e. a yield of about 5.5% relative to the dry weight of the rhizomes. This extract has a gingerol content which is generally greater than 75% (w/w).

EXAMPLE 6

DEODORANT ACTIVITY OF A CRUDE EXTRACT OF *ALPINIA GALANGA* RHIZOMES a) Systematic deodorant activity:

The systematic deodorant activity of a crude extract of *Alpinia galanga* rhizomes, prepared in accordance with Example 1, was tested on a group of 20 individuals by administering to them, via the oral route, this extract preformulated in the form of gel-capsules, and was compared with the activity of a placebo.

To do this, 1 kilogram of crude extract was intimately mixed with 1 kilogram of maltodextrin in a blade mill to ensure better homogeneity of the mixture and to obtain a mobile, non-sticky powder. This powder was then distributed in No. 0 gel-capsules so as to obtain a unit dosage of 250 mg of crude extract.

These gel-capsules were administered orally to a first group (group A) of 20 individuals comprising 10 men and 10 women between 17 and 62 years of age, for 10 days at a rate of 3 gel-capsules per day in a single intake, while a control group (group T), also composed of 10 men and 10 women and statistically comparable to the first, received, for 10 days and in a single oral intake, 3 gel-capsules per day each containing 250 mg of lactose.

The individuals of the two groups abstained from using local-application deodorants for the entire week preceding the start of the test, as well as throughout the duration of this test.

The efficacy of the crude extract in accordance with the invention and that of the placebo were evaluated by means of sensory analysis on the axillary zone of the individuals, in accordance with the tests conventionally used for deodorants, on the first day of the test (D0) before the first intake, on the 3rd and 6th days (D3 and D6), on the final day of the test (D10), as well as on the 3rd and 6th days following the end of this test (D13 and D16).

The results obtained expressed in the form of scores ranging from 0 to 5—the value 0 corresponding to an absence of deodorant efficacy and the value 5 to absolute deodorant efficacy (total absence of production of odours)—are given in Table 1 below.

TABLE 1

| DAY | GROUP A | GROUP T |
|-----|---------|---------|
| D0  | 0       | 0       |
| D3  | 2       | 0       |
| D6  | 4       | 0       |
| D10 | 4       | 1       |
| D13 | 3       | 0       |
| D16 | 0       | 0       | b) Local deodorant activity:

The local deodorant activity of a crude extract of *Alpinia galanga* rhizomes, prepared in accordance with Example 1, was also tested on a group of 20 individuals against placebo.

To do this, a first group (Group A) comprising 10 men and 10 women aged between 17 and 62 applied, by spraying onto the two axillary zones, for 3 days and at a rate of only one spray-application per day, 0.5 ml of a 50% ethanol solution comprising 1% of the said extract, while a second group (Group T) also composed of 10 men and 10 women and statistically comparable to the first, applied 0.5 ml of 50% ethanol under the same conditions.

All the individuals abstained from using local-application deodorants for the entire week preceding the start of the test, as well as throughout the duration of this test.

The efficacy of the crude extract in accordance with the invention and that of the placebo, were evaluated by means of sensory analysis of the axillary zone of the individuals, on the first day of the test before the first application (T0) and then 24 hours (T24), 48 hours (T48) and 72 hours (T72) after the start of this test.

The results, expressed in the form of scores ranging from 0 to 5—the value 0 corresponding to an absence of deodorant efficacy and the value 5 to absolute deodorant efficacy—are given in Table 2 below.

TABLE 2

| HOURS | GROUP A | GROUP T |
|-------|---------|---------|
| T0    | 0       | 0       |
| T24   | 2       | 0       |
| TD48  | 3       | 0       |
| T72   | 3       | 0       |

EXAMPLE 7

DEODORANT ACTIVITY OF [3]-SHOGAOL a) Systemic deodorant activity:

The systemic deodorant activity of [3]-shogaol was checked on a group of 20 individuals (Group A) against placebo (Group T) by means of a test similar to the one used according to Example 6 a) for evaluating the systemic efficacy of the crude extract of *Alpinia galanga* rhizomes, the only difference being that these individuals received gel-capsules containing 25 mg of [3]-shogaol instead of receiving gel-capsules containing 250 mg of the said extract.

The results obtained, also expressed in the form of scores ranging from 0 (absence of efficacy) to 5 (absolute efficacy), are given in Table 3 below.

TABLE 3

| DAY | GROUP A | GROUP T |
|-----|---------|---------|
| D0  | 0       | 0       |
| D3  | 4       | 1       |
| D6  | 5       | 0       |
| D10 | 5       | 1       |
| D13 | 4       | 0       |
| D16 | 1       | 0       | b) Local deodorant activity:

Preparation of a cosmetic solution of [3]-shogaol which can be used as a local deodorant:

10 g of [3]-shogaol are dissolved in 250 ml of 96% ethanol without heating. When dissolution is complete, 50 ml of monopropylene glycol and 200 ml of purified water are added. The solution obtained is filtered and then packaged in spray-containers.

Evaluation of the efficacy of the cosmetic solution of [3]-shogaol:

This was performed on a group of 20 individuals (Group A) versus placebo (Group T) by means of a test similar to the one used in Example 6 b) for assessing the deodorant activity which the crude extract of *Alpinia galanga* is capable of exhibiting locally.

However, in the present evaluation, the individuals of Group A applied, at each spray-application, 0.5 ml of cosmetic solution of [3]-shogaol while the individuals of Group T applied 0.5 ml of an ethanolic solution containing 10% monopropylene glycol and 40% water.

The results obtained during this evaluation, also expressed in the form of scores ranging from 0 (absence of efficacy) to 5 (absolute efficacy), are given in Table 4 below.

TABLE 4

| HOURS | GROUP A | GROUP T |
|-------|---------|---------|
| T0    | 0       | 0       |
| T24   | 4       | 0       |
| T48   | 4       | 1       |
| T72   | 5       | 0       |

EXAMPLE 8

DEODORANT ACTIVITY OF A CRUDE EXTRACT OF *ZINGIBER OFFICINALIS* RHIZOMES a) Systemic deodorant activity:

The systemic deodorant activity of a crude extract of *Zingiber officinalis* rhizomes, prepared in accordance with Example 4, was tested on a group of 20 individuals (Group A) versus placebo (Group T) by means of a test similar to the one used in Example 6 a) for evaluating the systemic efficacy of the crude extract of *Alpinia galanga* rhizomes.

The results obtained, also expressed in the form of scores ranging from 0 (absence of efficacy) to 5 (absolute efficacy) are given in Table 5 below.

TABLE 5

| DAY | GROUP A | GROUP T |
|-----|---------|---------|
| D0  | 0       | 0       |
| D3  | 2       | 0       |
| D6  | 2       | 0       |
| D10 | 3       | 1       |
| D13 | 2       | 0       |
| D16 | 0       | 0       | b) Local deodorant activity:

The local deodorant activity of a crude extract of *Zingiber officinalis*, prepared in accordance with Example 4, was also tested on a group of 20 individuals (Group A) versus placebo (Group T) by means of a test similar to the one used in Example 6 b) for evaluating the deodorant efficacy which the crude extract of *Alpinia galanga* is capable of exhibiting locally.

The results, also expressed in the form of scores ranging from 0 (absence of efficacy) to 5 (absolute efficacy), are given in Table 6 below.

TABLE 6

| HOURS | GROUP A | GROUP T |
|-------|---------|---------|
| T0    | 0       | 0       |
| T24   | 2       | 0       |
| T48   | 2       | 0       |
| T72   | 2       | 0       |

EXAMPLE 9

DEODORANT ACTIVITY OF A PURIFIED EXTRACT OF *ZINGIBER OFFICINALIS* RHIZOMES b) Systemic deodorant activity:

The systemic deodorant activity of a purified extract of *Zingiber officinalis* rhizomes, prepared in according with Example 5, was checked on a group of 20 individuals (Group A) versus placebo (Group T) by means of a test similar to the one used according to Example 6 a) for evaluating the systemic efficacy of the crude extract of *Alpinia galanga* rhizomes, the only difference being that these individuals received gel-capsules containing 25 mg of purified extract of *Zingiber officinalis* rhizomes instead of receiving gel-capsules containing 250 mg of crude extract of *Alpinia galanga* rhizomes.

The results obtained, also expressed in the form of scores ranging from 0 (absence of efficacy) to 5 (absolute efficacy), are given in Table 7 below.

TABLE 7

| DAY | GROUP A | GROUP T |
|-----|---------|---------|
| D0  | 0       | 0       |
| D3  | 3       | 1       |
| D6  | 3       | 0       |
| D10 | 4       | 1       |
| D13 | 2       | 0       |
| D16 | 1       | 0       | b) Local deodorant activity:

Preparation of a cosmetic solution from a purified extract of *Zingiber officinalis* which can be used as a local deodorant:

10 g of a purified extract, prepared in accordance with Example 5, are dissolved in 250 ml of 96% ethanol without heating. When dissolution is complete, 50 ml of monopropylene glycol and 200 ml of purified water are added. The solution obtained is filtered and then packaged in spray-containers.

Evaluation of the efficacy of the said cosmetics solution:

This was performed on a group of 20 individuals (Group A) versus placebo (Group T) by means of a test similar to the one used according to Example 6 b) for assessing the deodorant activity which the crude extract of *Alpinia galanga* rhizomes is capable of exhibiting locally.

However, in the present evaluation, the individuals of Group A applied, at each spray-application, 0.5 ml of cosmetic solution, while the individuals of Group T applied 0.5 ml of an ethanolic solution containing 10% monopropylene glycol and 40% water.

The results obtained during this evaluation, also expressed in the form of scores ranging from 0 (absence of efficacy) to 5 (absolute efficacy) are collated in Table 8 below.

TABLE 8

| HOURS | GROUP A | GROUP T |
|-------|---------|---------|
| T0    | 0       | 0       |
| T24   | 3       | 0       |
| T48   | 2       | 1       |
| T72   | 3       | 0       |

As emerges from the account hereinabove, the invention is not limited in any way to the methods for forming it, implementing it and applying it which have just been described in greater detail: on the contrary, it embraces all the variants thereof which may occur to a person skilled in the art, without departing from the context or scope of the present invention.

Thus, the use of any shogaol or gingerol which would be obtained synthetically for the prepartion of a deodorant composition, and any deodorant composition containing such a shogaol or gingerol, also falls within the context of the invention.

What is claimed is:

1. A method for suppressing body odors in a human comprising administering orally to said human or applying to the skin of said human, at least one compound chosen from the group which consists of shogaols and gingerols.

2. A method according to claim 1, wherein the compound corresponds to the general formula (I):
in which X represents:

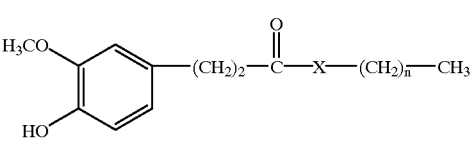

(I)

either —CH═CH—, in which case n is equal to 1, 2, 4, 6, or 8;

—CH$_2$—CH(OH)—, in which case n is equal to 2, 4, 6 or 8.

3. A method according to claim 1, wherein the compound is used in the form of a crude or purified extract of a plant belonging to the Zingiberacea family, the said extract optionally being combined with one or more other active substances and/or one or more suitably selected excipients.

4. A method according to claim 3, wherein said crude extract contains an amount of compound between 1 and 5% by weight relative to the dry weight of the said extract.

5. A method according to claim 3, wherein the crude extract of the plant belonging to the Zingiberacea family is obtained from fresh or dry rhizomes of the said plant:

by macerating ground material of these rhizomes at a temperature of between 10 and 35° C., followed by one or more extractions of this ground material at reflux, or by subjecting ground material of the said rhizomes to percolation at a temperature of between 10 and 35° C., each of these operations (maceration, extractions at reflux and percolation) being performed using a suitable organic solvent or a mixture of suitable organic solvent and, if desired, by removing the solvent(s) from the extract thus obtained in order to obtain a dry extract.

6. A method according to claim 3, wherein the purified extract contains an amount of compound at least equal to 75% by weight relative to the dry weight of said extract.

7. A method according to claim 5, wherein the purified extract of the plant belonging to the Zingiberacea family is obtained:

by subjecting said crude extract, after optional removal of the solvent(s) it contains and/or its uptake in water, to one or more counter-current extractions using a water-immiscible organic solvent or a mixture of water-immiscible organic solvents and, removing the solvent(s) from the extract thus obtained in order to obtain a dry extract.

8. A method according to claim 3, wherein the plant of the Zingiberacea family is chosen from the group consisting of the species *Alpina galanga, Alpinia officinarum, Zingiber officinalis, Zingiber cassumunar* and *Zingiber zerumbet*.

9. A method according to claim 1, wherein said at least one compound is contained in a pharmaceutical composition comprising the compound as active principle, optionally combined with one or more other active principles, and at least one pharmaceutically acceptable excipient.

10. A method according to claim 1, wherein said at least one compound is contained in a cosmetic composition comprising the compound as active substance, optionally combined with one or more other active substances, and at least one suitable selected excipient.

11. A method according to claim 1, wherein said at least one compound is contained in a dietary composition comprising the compound as active substance, optionally combined with one or more other active substances, and at least one suitable selected excipient.

12. A shogaol corresponding to the general formula:

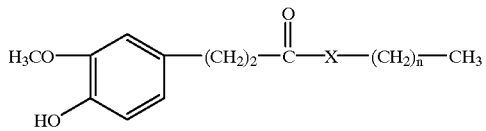

in which X represents —CH═CH— and n is equal to 1.

13. A crude extract of a plant belonging to the genus Alpinia, wherein said extract contains an amount of shogaol according to claim 12 of between about 1% and about 5% by weight relative to the dry weight of the said extract.

14. A crude extract according to claim 13, wherein said extract is obtained from fresh or dry rhizomes of the said plant:

by macerating ground material of these rhizomes at a temperature of between 10 and 35° C., followed by one or more extractions of this ground material at reflux, or by subjecting ground material of the said rhizomes to percolation at a temperature of between 10 and 35° C., each of these operations (maceration, extractions at reflux and percolation) being performed using a suitable organic solvent or a mixture of suitable organic solvents and, if desired, by removing the solvent(s) from the extract thus obtained in order to obtain a dry extract.

15. A crude extract according to claim 13, wherein said extract is an extract of *Alpinia galanga*.

16. A purified extract of a plant belonging to the genus Alpinia, wherein said extract contains an amount of shogaol according to claim 12 at least equal to 75% by weight relative to the dry weight of the said extract.

17. A purified extract according to claim 16, wherein said extract is obtained:

by subjecting a crude extract of a plant belonging to the genus Alpinia, after optional removal of the solvent(s) it contains and/or its uptake in water, to one or more counter-current extractions using a water-immiscible organic solvent or a mixture of water-immiscible organic solvents and, if desired, by removing the solvent(s) from the extract thus obtained in order to obtain a dry extract.

18. A purified extract according to claim 16, wherein said extract is an extract of *Alpinia galanga*.

19. A deodorant composition comprising a shogaol according to claim 12 as active substance.

20. A deodorant composition according to claim 19, wherein said composition is a pharmaceutical composition which comprises [3]-shogaol as active principle, optionally combined with one or more other active principles and at least one pharmaceutically acceptable excipient.

21. A deodorant composition according to claim 19, wherein said composition is a cosmetic composition which comprises [3]-shogaol as active substance, optionally combined with one or more other active substances, and at least one suitably selected excipient.

22. A deodorant composition according to claim 19, wherein said composition is a dietary composition which comprises [3]-shogaol as active substance, optionally combined with one or more other active substances, and at least one suitable selected excipient.

* * * * *